(12) United States Patent
Reddy et al.

(10) Patent No.: US 7,296,927 B2
(45) Date of Patent: Nov. 20, 2007

(54) LABORATORY APPARATUS AND METHOD FOR EVALUATING CEMENT PERFORMANCE FOR A WELLBORE

(75) Inventors: B. Raghava Reddy, Duncan, OK (US); Dennis W. Gray, Comanche, OK (US); Johnny W. Johnson, Duncan, OK (US); Anthony V. Palmer, Ardmore, OK (US); Keith E. Blaschke, Duncan, OK (US); Lance E. Brothers, Chickasha, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 11/100,999

(22) Filed: Apr. 7, 2005

(65) Prior Publication Data

US 2006/0225523 A1   Oct. 12, 2006

(51) Int. Cl.
*G01N 3/00* (2006.01)
(52) U.S. Cl. .................................................. 374/47
(58) Field of Classification Search ................. 73/803; 374/47
See application file for complete search history.

(56) References Cited

U.S. PATENT DOCUMENTS

| | | | |
|---|---|---|---|
| 4,408,489 A * | 10/1983 | Spangle | 73/866 |
| 4,538,452 A * | 9/1985 | Hrvojic | 73/61.64 |
| 4,567,759 A | 2/1986 | Ekstrom et al. | |
| 4,607,530 A | 8/1986 | Chow | |
| 4,648,264 A | 3/1987 | Freese et al. | |
| 4,685,092 A | 8/1987 | Dumont | |
| 4,703,427 A | 10/1987 | Catala et al. | |
| 4,757,479 A | 7/1988 | Masson et al. | |
| 4,809,237 A | 2/1989 | Vogel et al. | |
| 4,823,594 A | 4/1989 | Gray | |
| 4,848,145 A | 7/1989 | Blaschke et al. | |
| 4,893,285 A | 1/1990 | Masson et al. | |
| 4,896,303 A | 1/1990 | Leslie et al. | |
| 4,970,695 A | 11/1990 | Huau | |
| 5,089,989 A | 2/1992 | Schmidt et al. | |
| 5,127,473 A | 7/1992 | Harris et al. | |
| 5,216,638 A | 6/1993 | Wright | |
| 5,233,863 A | 8/1993 | Surjaatmadja et al. | |
| 5,353,637 A | 10/1994 | Plumb et al. | |
| 5,377,160 A | 12/1994 | Tello et al. | |
| 5,696,059 A | 12/1997 | Onan et al. | |

(Continued)

FOREIGN PATENT DOCUMENTS

EP   0 443 936 A1   8/1991

OTHER PUBLICATIONS

John W. Minear and K. Joe Goodwin, "*Cement-Sheath Evaluation*," Chapter 10, *Petroleum Well Construction*, John Wiley & Sons Publisher, ISBN 0-471-96938-9, copyright 1998, pp. 271-296.

*Primary Examiner*—Robert Raevis
(74) *Attorney, Agent, or Firm*—John W. Wustenberg; Fish & Richardson P.C.

(57) ABSTRACT

A test cell for testing a sample cement composition includes a test chamber and a variable stress system. The test chamber is configured to hold a sample cement composition for a wellbore. The variable stress system communicates with the test chamber. Performance of the sample cement composition is tested for a wellbore using the variable stress system.

11 Claims, 6 Drawing Sheets

U.S. PATENT DOCUMENTS

| | | |
|---|---|---|
| 5,763,773 A | 6/1998 | Birchak et al. |
| 5,869,750 A | 2/1999 | Onan et al. |
| 6,055,874 A | 5/2000 | Onan et al. |
| 6,070,662 A | 6/2000 | Ciglenec et al. |
| 6,484,568 B1 | 11/2002 | Griffith et al. |
| 6,644,402 B1 | 11/2003 | Sharma et al. |
| 6,782,735 B2 | 8/2004 | Walters et al. |
| 6,818,596 B1* | 11/2004 | Hayes ........................ 507/120 |
| 6,829,922 B2 | 12/2004 | Patin et al. |
| 2003/0140707 A1* | 7/2003 | Pyle et al. .................... 73/808 |
| 2003/0150263 A1 | 8/2003 | Economides et al. |
| 2003/0221829 A1 | 12/2003 | Patel et al. |
| 2004/0054262 A1* | 3/2004 | Horak ........................ 600/300 |
| 2004/0154263 A1* | 8/2004 | Li et al. .................... 52/720.1 |
| 2005/0126300 A1* | 6/2005 | Go Boncan et al. .......... 73/803 |
| 2005/0152432 A1* | 7/2005 | Hakimuddin ................ 374/53 |
| 2007/0082822 A1* | 4/2007 | Kirsner et al. ............. 507/100 |

* cited by examiner

LABORATORY APPARATUS AND METHOD FOR EVALUATING CEMENT PERFORMANCE FOR A WELLBORE

TECHNICAL FIELD

Slurry design for subterranean cementing operation, and more particularly, to a laboratory apparatus and method for evaluating cement performance and design of cement composition for a wellbore.

BACKGROUND

Oil and gas wells extend from the surface to one or more subterranean formations of rock containing oil and/or gas. The well is typically cased by cementing a steel or other suitable casing in the wellbore. The casing stabilizes the sides of the wellbore, prevents pollution of fresh water reservoirs and/or prevents fluids from zones other than oil and gas producing zones from entering the wellbore.

Cementing operations pump wet cement slurry down a wellbore to fill the space between the casing and the rock walls. The cement protects the casing and prevents water and other fluids from flowing vertically in the space between the casing and rock walls of the wellbore. Typically, cementing operations are designed and supervised by engineers. Laboratory technicians test and select the cement slurry and additives.

Cement compositions are designed for a variety of wellbore conditions, which may vary in depth, temperature and pressure. In designing a cement composition for a wellbore, a number of potential slurries are typically tested in a laboratory for pumpability, safe placement time and compressive strength. The compressive strength is used as a measure of the ability of the cement composition to provide long-term zonal isolation. Field observations have shown that during life of the well many cemented wells failed as seen by buildup of pressure behind a cemented pipe, leakage of fluids from the formation into the wellbore via cracks and from channels generated in areas where the cement debonded from the casing or formation. Such problems may be remedied by squeezing sealants, such as cement slurries or silicate fluids, into the flowpaths and allowing them to set. Cement sheath failure may be due to cyclical pressure and temperature changes experienced by cement sheath from various well operations such as completion, pressure testing, fracturing and remedial operations. Simulation of cement sheath durability in realistic, large-scale wellbore models has been performed using a full-scale wellbore model in which cement is pumped between a full-size liner and a pipe representing the subterranean formation of the wellbore. The full-scale models have been performance tested by cycling pressure and temperature under wellbore conditions.

SUMMARY

Laboratory apparatus and method are provided for evaluating cement performance for a wellbore. In accordance with one embodiment, a test cell for testing a sample cement composition includes a test chamber configured to hold a sample cement composition for a wellbore. A variable stress system communicates with the test chamber. Performance of the sample cement composition for a wellbore is tested using the variable stress system.

In accordance with one or more specific embodiments, the variable stress system may comprise a variable pressure system operable to cycle a pressure applied to the sample cement composition. In an another embodiment, the variable pressure system may comprise a variable temperature system operable to cycle the temperature applied to the sample cement composition. In these and other embodiments, the test cell may apply cyclic pressure and/or temperature changes to the sample cement composition during curing of the sample cement composition and/or after curing of the sample cement composition.

Technical advantages of one, some, all or none of the embodiments may include providing a laboratory screening test capable of applying cyclical stress to various sample cement compositions by varying pressure and/or temperature applied to the sample cement compositions and testing cement shrinkage, durability and/or other properties. A reusable cell may be used for the laboratory screening to reduce cost and/or allow screening of a larger number of sample cement compositions. Accordingly, slurry design for a wellbore may be improved.

The details of one or more embodiments of the laboratory apparatus and method for evaluating cement performance for a wellbore are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
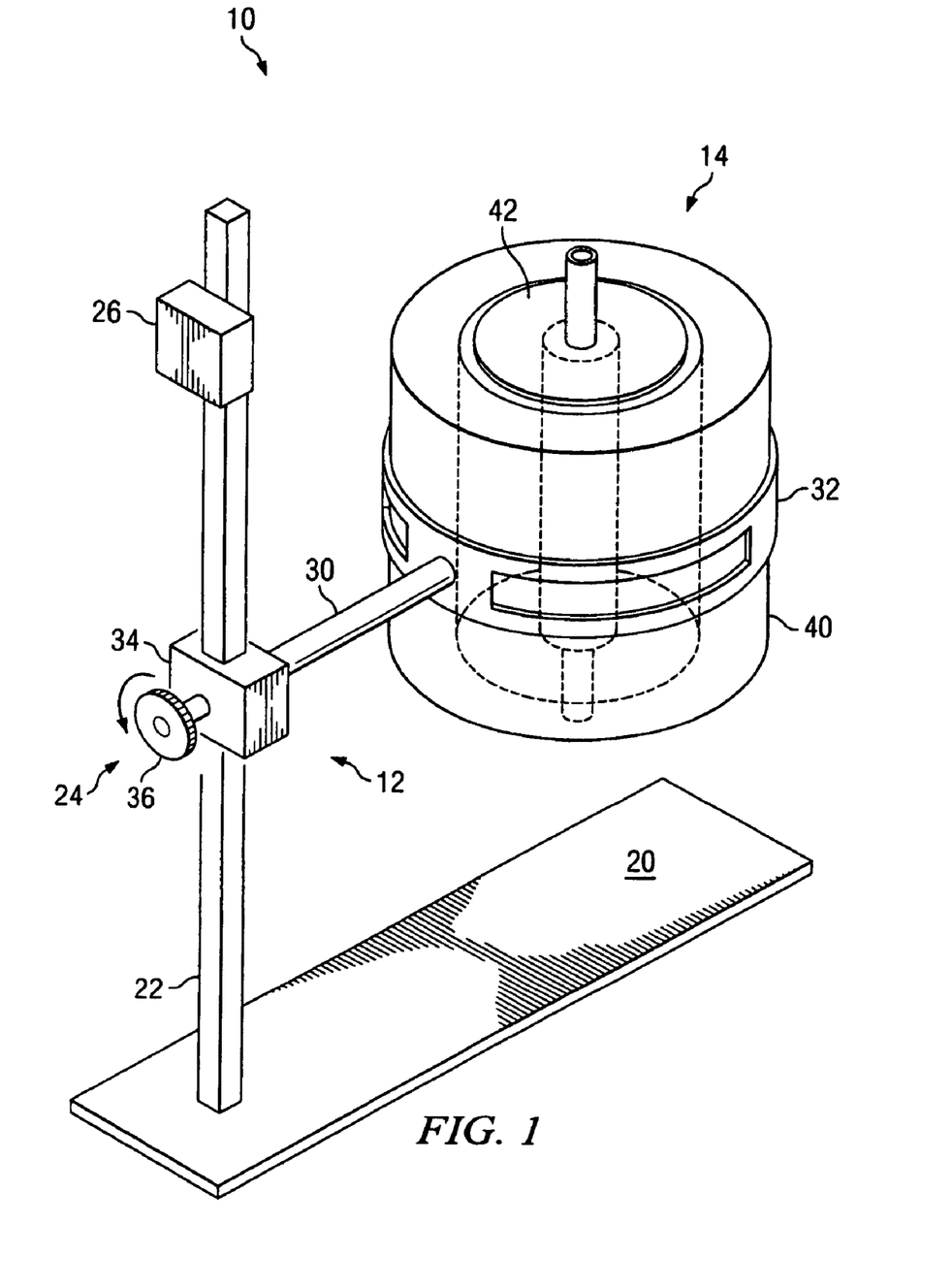
FIG. 1 is a schematic view illustrating one embodiment of a laboratory apparatus for evaluating cement performance for a wellbore.

FIG. 1 illustrates one embodiment of a laboratory apparatus 10 for evaluating cement performance for a wellbore. The laboratory apparatus 10 may perform laboratory screening test for a number of sample cement compositions to determine performance of the sample cement compositions for the wellbore. Performance for a wellbore includes performance under conditions simulating, matching, based on, designed for or otherwise corresponding to those in or expected in the wellbore. The screening tests may allow a relatively large number of sample cement compositions to be tested for cement shrinkage, durability and/or other performance characteristics. For example, screening test may be performed on one or more sample cement compositions, for example, 10, 15, 20, 30 or more, in an initial stage of slurry design for the wellbore. The laboratory apparatus 10 may be any suitable device in which sample cement compositions may be tested in scaled-down form under variable stress conditions.

Referring to FIG. 1, the laboratory apparatus 10 comprises a stand 12 and a simulated wellbore assembly 14. The stand 12 may include a base 20, spine 22, rotating arm 24 and a controller 26. The rotating arm 24 may comprise an arm 30 coupled to a clamp 32. The base 20, spine 22, and rotating arm 24 may comprise steel or other suitable materials for supporting the simulated wellbore assembly 14.

The clamp 32 secures the simulated wellbore assembly 14 to the arm 30. A bearing block 34 allows rotation of the arm 30 through the spine 22. A handle 36 may be provided at the end of the arm 30 to facilitate rotation of the simulated wellbore assembly 14. The handle 36 and/or bearing block 34 may include a lock for securing the simulated wellbore assembly 14 at various angles. For example, the simulated wellbore assembly 14 may be secured with its top up, down, or at other intermediate angles.

Controller 26 includes a centralized processing unit (CPU) or other suitable electronics for controlling and monitoring screening test performed in the simulated wellbore assembly 14. In one embodiment, the controller 26 may control pressure changes, temperature changes or other variable stress conditions applied to a sample cement composition in the simulated wellbore assembly 14. The variable stress conditions may be any variable force or condition applied to a sample cement composition in cured or uncured form that test performance over time. The variable stress conditions may be cyclic in that they recur in or are marked by cycles. The controller 26 may communicate with the one or more variable stress systems that apply the variable stress conditions and/or other test equipment over wireline or wireless links.

The simulated wellbore assembly 14 may comprise a temperature block 40 and a test cell 42. The temperature block of 40 may raise, lower, cycle or otherwise vary temperatures applied to an exterior of the test cell 42. The temperature block 40 may comprise ceramic, metal and/or other suitable material. The temperature block 40 may include an internal heating and/or cooling element or may comprise heating and cooling coils which may be connected to a temperature bath for temperature control.

The test cell 42 receives and holds a sample cement compositions for a screening test. The test cell 42, as described in more detail below in connection with FIG. 2, includes ports for measuring cement shrinkage and durability. Durability comprises sheath failure, other permeability changes and/or other long-term performance criteria in response to pressure changes, temperature changes, or other stress variations. In one embodiment, the test cell 42 is completely reusable. In another embodiment, at least a portion of test cell 42 is reusable.

Figure 2:
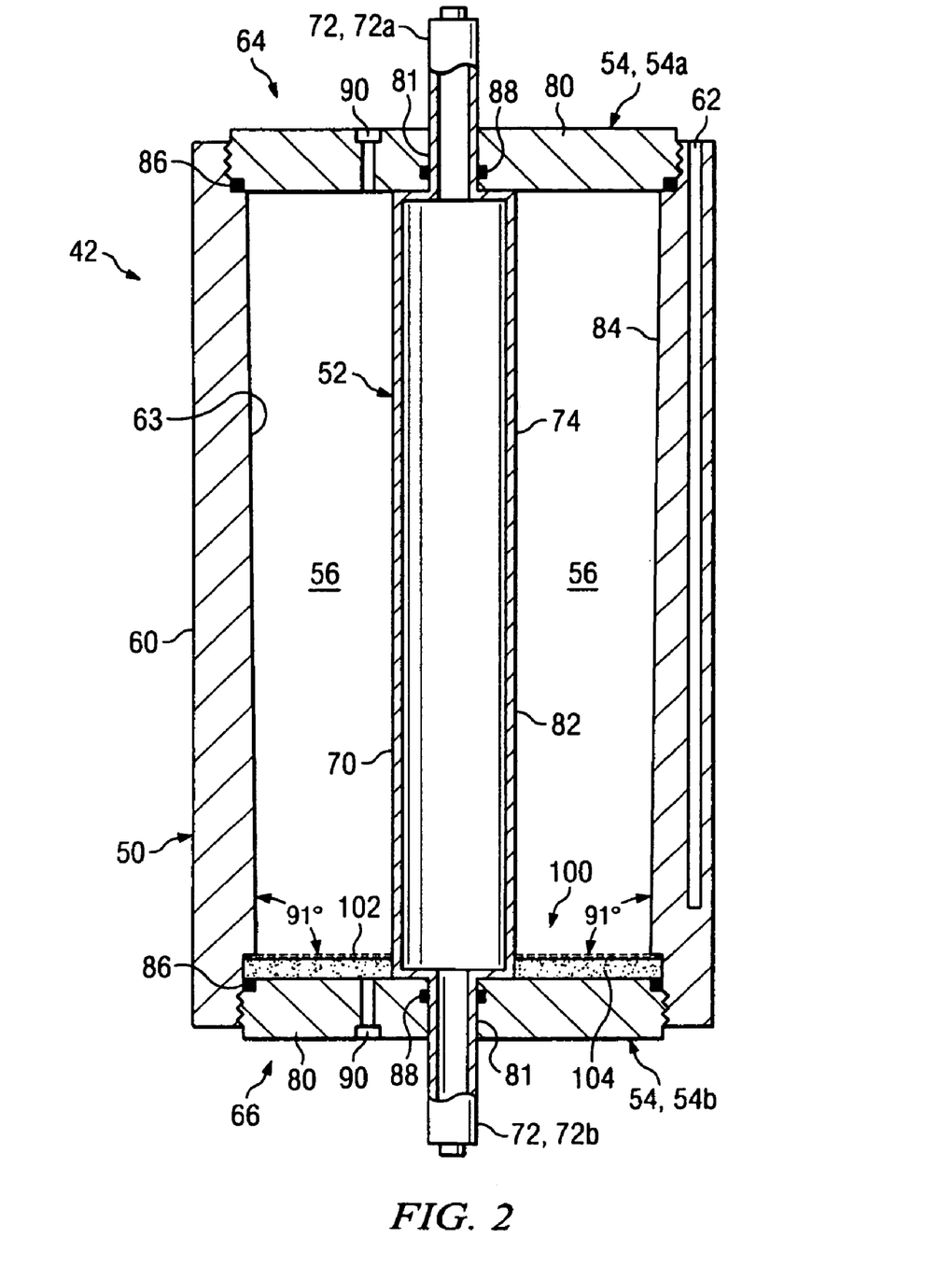
FIG. 2 is a cross-sectional view illustrating one embodiment of the test cell for the laboratory apparatus of FIG. 1.

FIG. 2 illustrates one embodiment of the test cell 42. The test cell 42 may be any device in which a sample cement composition can be evaluated under variable stress conditions. In the illustrated embodiment, the test cell 42 comprises a pipe-in-pipe configuration and is reusable. The test cell 42 may be otherwise suitably configured and may be for one, several or many screening tests.

Referring to FIG. 2, the test cell 42 includes an outer pipe 50, an inner pipe 52, and end caps 54. End caps 54 may comprise a top end cap 54a and a bottom end cap 54b. The outer pipe 50, inner pipe 52 and end caps 54 together form a test chamber 56 for receiving, holding and testing sample cement compositions.

The outer pipe 50 may comprise a sleeve having an elongated cylindrical body 60. A thermocouple well 62 may be formed in the elongated cylindrical body 60. In one embodiment, an inner wall 63 of the elongated cylindrical body 60 may be straight or taper inwardly to facilitate removal of a sample cement composition from the test chamber 56 after testing. For example, the inner wall 63 may taper inwardly from a top 64 of the test cell 42 to a bottom 66 of the test cell 42. The taper may be a fraction of a degree up to, for example, several degrees. In the illustrated embodiment, the taper is one degree.

The elongated cylindrical body 60 may be formed of metallic, plastic, or other suitable material operable to communicate variable stress conditions to a sample cement composition in the test chamber 56. In a particular embodiment, the elongated cylindrical body 60 comprises steel or other metal operable to readily communicate temperature changes from the temperature block 40 to the sample cement composition in the test chamber 56.

The inner pipe 52 may comprise an elongated cylindrical body 70. In one embodiment, the elongated cylindrical body 70 may comprise stems 72 extending from an intermediate section 74 through the end caps 54. In particular, a top stem 72a may extend through the top end cap 54a and a bottom stem 72b may extend through the bottom end cap 54b. The intermediate section 74 may have a diameter enlarged from that of the stems 72 to, for example, more accurately simulate casing in a wellbore, control the area of the test chamber 56 to which pressure and/or temperature changes are applied and/or to control dimensions of the test chamber 56. The stems 72 may each comprise external threads for coupling to a pipe, line or other suitable device. Other pressure tight connectors may be used. For example, clamps or quick connects may be used.

The elongated cylindrical body 70 may comprise metallic, plastic or other suitable material operable to communicate variable stress conditions to the sample cement composition in the test chamber 56. In a particular embodiment, the elongated cylindrical body 70 may comprise PVC operable to communicate both pressure and temperature changes to the test chamber 56.

End caps 54 secure the inner pipe 52 in the outer pipe 50. In one embodiment, the end caps 54 each comprise a circular body 80 with a central orifice 81 through which the corresponding stem 72 of the inner pipe 52 extends. The central orifices 81 may be formed to maintain the inner pipe 52 concentrically within the outer pipe 50. In this embodiment, an inner wall 82 and an outer wall 84 of the test chamber 56 may be concentric. The end caps 54 may comprise steel, plastic or other suitable material.

The end caps 54 may be threaded onto or be otherwise fastened to the outer pipe 50. The end caps 54 may each include an outer seal 86 extending around the outer perimeter of the circular body 80 to provide a seal between the end cap 54 and the outer pipe 50. End caps 54 may also each include an inner seal 88 extending around the central orifice 81 in circular body 80 to provide a seal between the end cap 54 and the stem 72 extending through the end cap 54. The outer seal 86 and inner seal 88 may each comprise o-rings or other suitable seals operable to form a pressure tight seal for the test chamber 56. In one embodiment, the test chamber 56 may be safely operated up to a pressure of 10,000 psi.

Ports 90 may be formed in each of the end caps 54 to allow fluid communication with the test chamber 56 during testing. For example, ports 90 provide a fluid inlet and outlet for sheath failure and other permeability change measurements. The ports 90 may also be used for cement shrinkage measurements by connection to a graduated fluid level measuring device. The ports 90 may each comprise internal threads for connection to an external pipe, hose, line or other suitable device. Other pressure tight connectors may be used.

The test chamber 56 may, in the embodiment in which the inner and outer pipes 52 and 50 are concentric, be annular. In this embodiment, the test chamber 56 may simulate the space of a wellbore between a casing represented by the inner pipe 52 and a formation represented by outer pipe 50. In a particular embodiment, the test chamber 56 may have, for example, a length of between twelve (12) inches and twenty-four (24) inches, an outer diameter of three (3) to six (6) inches and an inner diameter of two (2) to four (4) inches. The test chamber 56 may be otherwise suitably configured, sized and shaped. For example, the test chamber 56 may have a length/diameter ratio of 3 to 12 and an outer diameter of 2 to 3 times the inner diameter.

A distributor 100 may be disposed at the bottom of the test chamber 56 in a notch formed in the elongated cylindrical body 60 of the outer pipe 50. The distributor 100 evenly, or substantially evenly, distributes fluid received from port 90 of the bottom end cap 54*b* across a base of the sample cement composition in the test chamber 56. In one embodiment, the distributor 100 comprises a mesh screen 102 and sand 104. The mesh screen 102 maintains the sand 104 in place. The mesh screen 102 may, for example, comprise a 325-mesh screen. Other suitable mesh screens 102 and high permeability materials may be used. In addition, other suitable structures may be used for distributor 100.

In operation, the test cell 42 may be assembled bottom side up first, for example, by placing the mesh screen 102 and sand 104 in the test chamber 56 and securing the bottom end cap 54*b* to the outer pipe 50. The test cell 42 may then be turned top side up. The inner pipe 52 may be disposed in the outer pipe 50 with the bottom stem 72*b* extending through the bottom end cap 54*b*. The sand 104 may be saturated with water and a sample cement composition poured into the test chamber 56 for testing. The top end cap 54*a* may then be secured to the outer pipe 50 with the top stem 72*a* extending through the top end cap 54*a*. The cement may be cured with or without a water cap on top of the sample cement composition.

Figure 3:
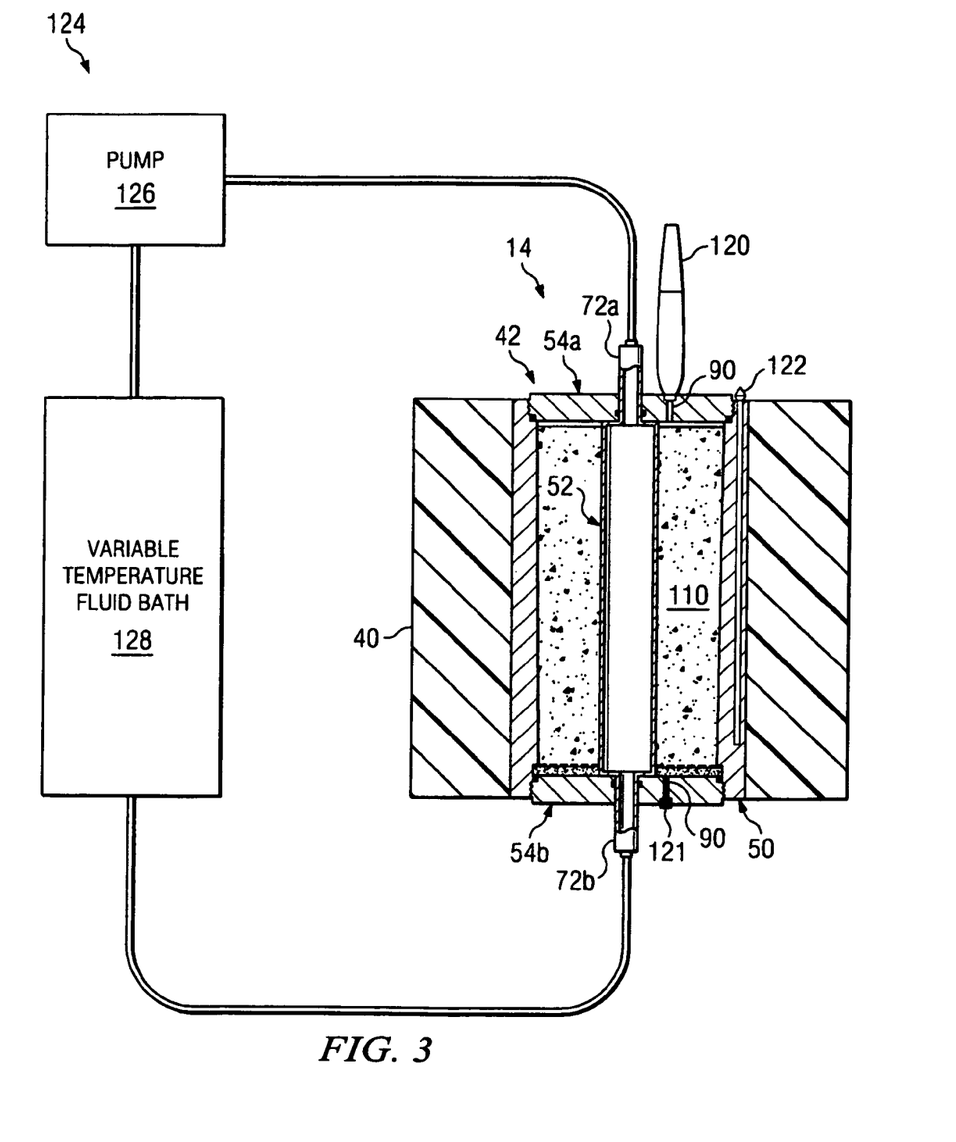
FIG. 3 is a schematic view illustrating one embodiment of a cement shrinkage test for a sample cement composition using the test cell of FIG. 2.
Figure 4:
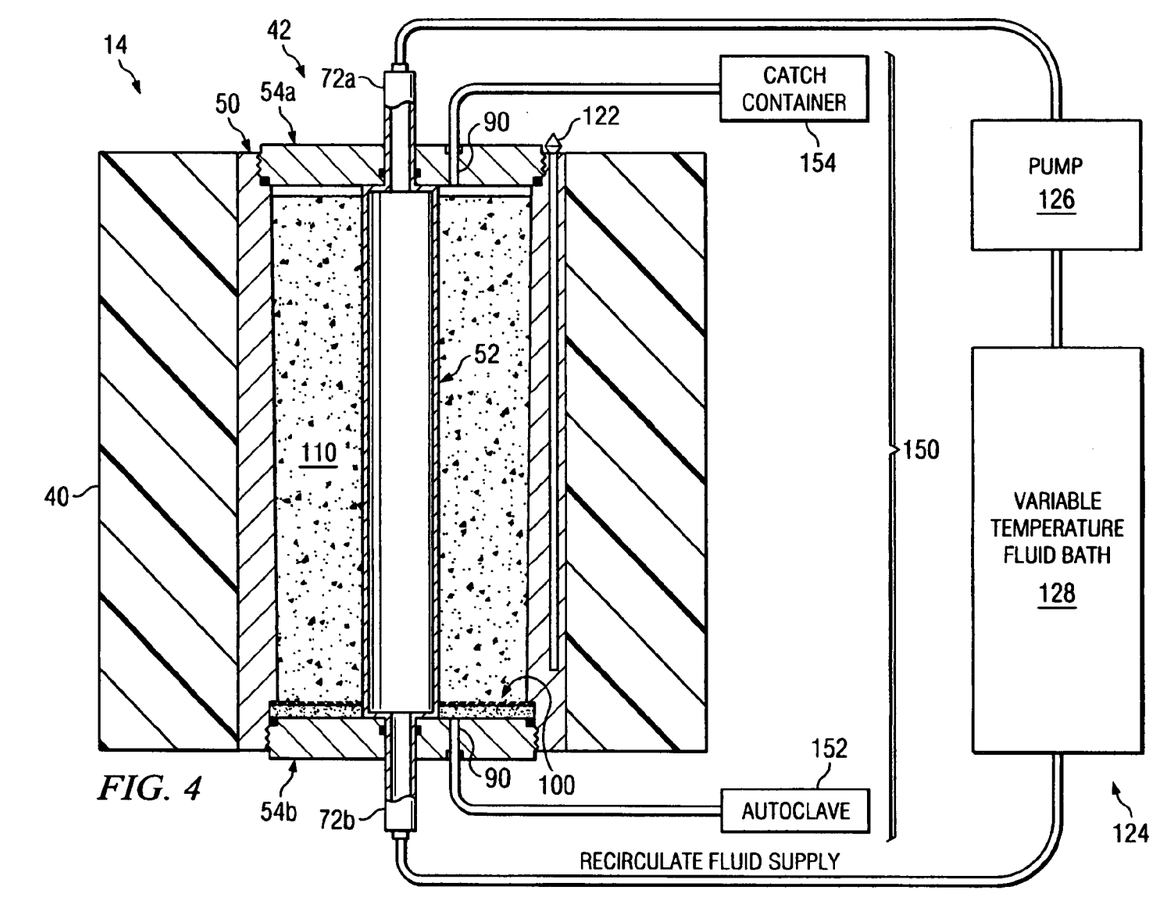
FIG. 4 is a schematic view illustrating one embodiment of a durability test for a sample cement composition using the test cell of FIG. 2.
Figure 5:
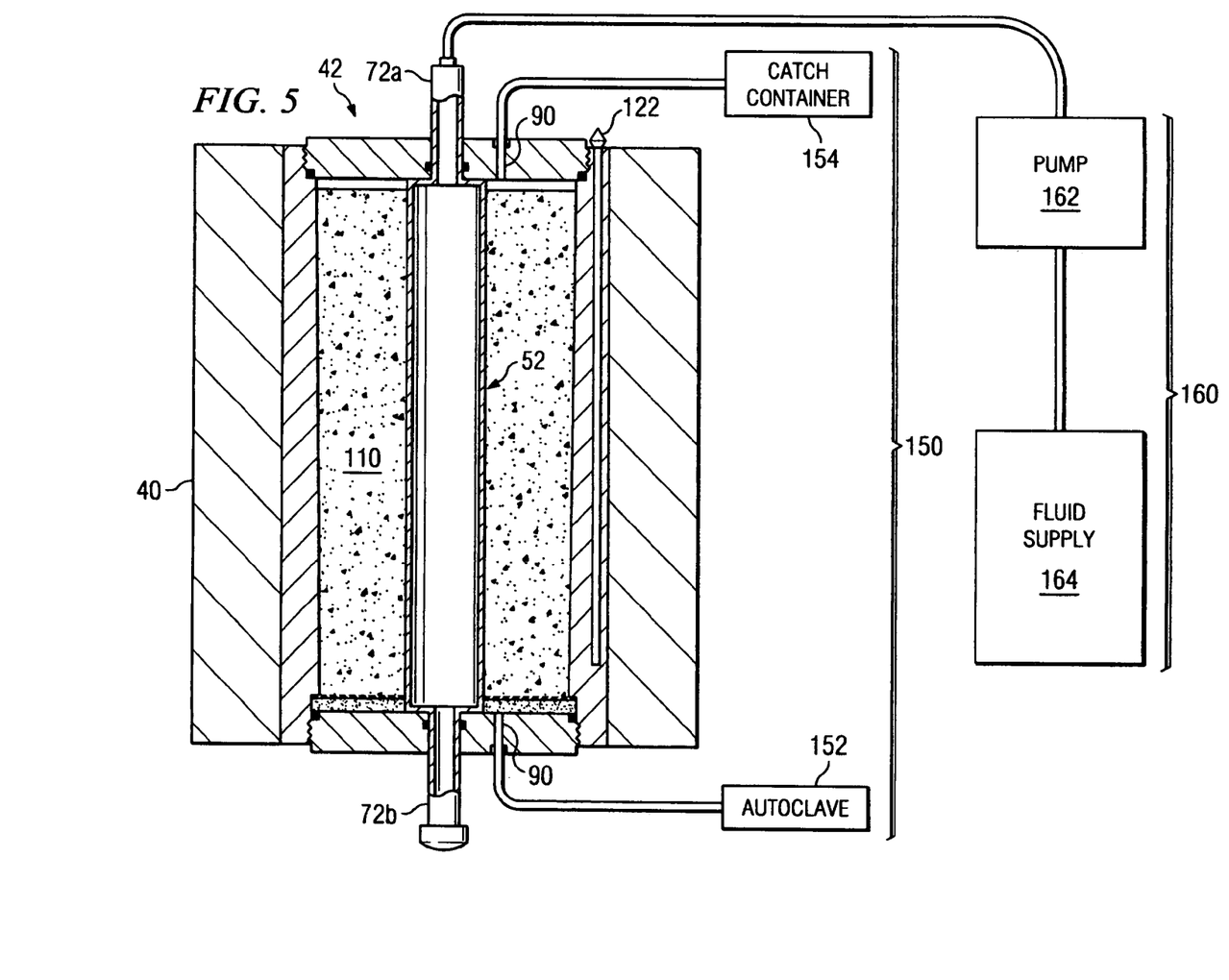
FIG. 5 is a schematic view illustrating another embodiment of a durability test for a sample cement composition using the test cell of FIG. 2.

The test cell 42 with the sample cement composition may be secured in the temperature block 40 of the simulated wellbore assembly 14 and the inner pipe 52 connected to variable pressure and/or temperature systems capable of varying pressure and/or temperature applied to the sample cement composition. Sheath failure, cement shrinkage and/or other test equipment may be connected to ports 90 for the screening test. FIGS. 3-5 illustrate various embodiments of screening test for the sample cement composition using the test cell 42.

FIG. 3 illustrates one embodiment of a cement shrinkage test for a sample cement composition 110 using the test cell 42. In this embodiment, the test cell 42 is set up and the sample cement composition 110 poured into the test cell 42 as previously described. Accordingly, the sample cement composition 110 will have an annular form. The test cell 42 is secured in the temperature block 40 to form the simulated wellbore assembly 14. Although not shown in FIG. 3, the simulated wellbore assembly 14 may be secured in the laboratory apparatus 10 for testing.

Referring to FIG. 3, a pipette 120 is connected to the port 90 of the top end cap 54*a*. The pipette 120 may contain dyed liquid and be graduated to allow fluid level changes to be easily monitored during the cement shrinkage test. The port 90 of the bottom end cap 54*b* may be plugged with plug 121. In another embodiment, the port 90 may be used to apply pressure during curing. A thermocouple 122 is secured in the thermocouple well 62. The thermocouple 122 may be connected to the controller 26 of the laboratory apparatus 10.

Inner pipe 52 is connected to a variable temperature system 124. In a particular embodiment, the top stem 72*a* of the inner pipe 52 is connected to an outlet of a circulating pump 126. An inlet of the circulating pump 126 is connected to an outlet of a variable temperature fluid bath 128. The bottom stem 72*b* of the inner pipe 52 is connected to a return of the variable temperature fluid bath 128. All connection may be by fluid and/or pressure tight piping and connectors. Fluid may be pumped from the variable temperature fluid bath 128 by circulating pump 126 to the inner pipe 52 and returned to variable temperature fluid bath 128. The variable temperature system 124 may comprise other or different suitable equipment. The variable temperature system 124 may be connected to and controlled by controller 26.

During the cement shrinkage test, temperature of the variable temperature system 124 and/or temperature block 40 are set and/or adjusted to a curing condition. The curing condition is a temperature change and/or other specific cure conditions for which the sample cement composition 110 is being designed. For example, the curing condition may also comprise a pressure change. In this embodiment, a back flow valve or other circulation and pressure control may be installed on the bottom stem 72*b* of the inner pipe 52 and the circulating pump 126 used to vary temperature and pressure in the inner pipe 52.

As the sample cement composition 110 cures, cement shrinkage may be measured by noting a drop in level of dye liquid in the pipette 120 as a function time. After curing is complete, the sample cement composition 110 may be tested for durability at an operational condition. The operational condition is a drilling, completion, production and/or other operational condition for which the sample cement composition 110 is being designed.

FIG. 4 illustrates one embodiment of a durability test for the sample cement composition 110 in the test cell 42. In this embodiment, sheath failure is tested under a variable temperature condition. Sheath failure is the change in permeability of the sample cement composition 110 to a fluid in response to a variable stress condition. Sheath failure may be tested immediately after completion of the cement shrinkage test, after curing of the sample cement composition 110 or other testing.

Referring to FIG. 4, test cell 42 is connected to the variable temperature system 124 as previously described in connection with FIG. 3. For the sheath failure test, the test cell 42 is also connected to a permeability test system 150. In a particular embodiment, the port 90 of the bottom end cap 54*b* is connected to an autoclave 152. The autoclave 152 may comprise a variable pressure autoclave containing dyed liquid. In another embodiment, the autoclave 152 may comprise gas or other suitable fluid. The port 90 of the top end cap 54*a* is connected to a dye catch container 154. In one embodiment, the dye catch container 154 may comprise a variable pressure container. In this embodiment, pressure differential between the autoclave 152 and the dye catch container 154 may be controlled to provide pressure differential across the axial length of the sample cement composition 110. The permeability test system 150 may comprise other suitable equipment. The permeability test system 150 may be connected to and controlled by controller 26.

For the sheath failure test, temperature of the temperature block 40 and/or variable temperature system 124 are set and/or adjusted to an operational condition. The temperature of the temperature block 40 may be set to correspond to that of the formation(s) surrounding the wellbore while the temperature of the variable temperature system 124 is cycled to match those of/or expected in the wellbore. Actual and/or expected temperature cycles of the wellbore may also be accelerated during testing.

During the sheath failure test, dye liquid flows from the autoclave 152 into distributor 100 and is distributed across the base of the sample cement composition 110. The dye liquid flows through any micro-annulus fractures, cracks or other permeability formed in the sample cement composition 110 during the sheath failure test. The sheath failure test may continue for a predetermined or other suitable period of time or until dye is observed in the dye catch container 154 indicating sheath failure of the sample cement composition 110.

Upon completion of the sheath failure test, the sample cement composition 110 may be removed from the test cell 42 and examined to determine the failure path. For example, the sample cement composition 110 may be sectioned and dye traces examined to determine failure path through the sample cement composition 110. The time until sheath failure for the sample cement composition 110 and/or failure path may be recorded and used to determine relative durability of the sample cement composition 110 to other sample cement compositions.

FIG. 5 illustrates another embodiment of a durability test for the sample cement composition 110 in the test cell 42. In this embodiment, sheath failure is tested under variable pressure conditions. As previously described in connection with FIG. 4, sheath failure may be tested immediately after completion of the cement shrinkage test, after curing of the sample cement composition 110 or otherwise.

Referring to FIG. 5, the test cell 42 is connected to a variable pressure system 160. In a particular embodiment, the top stem 72a of the inner pipe 52 is connected to an outlet of a volume control pump 162. An inlet of the volume control pump 162 is coupled to a fluid supply 164. The bottom stem 72b of the inner pipe 52 is capped. The volume control pump 162 may comprise a syringe pump, for example, an ISCO pump manufactured by Teledyne Isco, Inc., Lincoln, Nebr., or other suitable pump. The variable pressure system 160 may comprise other or different suitable equipment. The variable pressure system 160 may be connected to and controlled by controller 26. The ports 90 are connected to the permeability test system 150 as previously described in connection with FIG. 4.

For the sheath failure test, pressure in the inner pipe 52 and temperature of the temperature block 40 may be set and/or adjusted to an operational condition. The volume control pump 162 pumps fluid from fluid supply 164 to regulate pressure in the inner pipe 52 and thus applied to the sample cement composition. For example, pressure cycling may match those of the wellbore or be otherwise suitably based on those of the wellbore.

As previously described in connection with FIG. 4, sheath failure testing may continue for a specified or other suitable period of time or until dye is observed in the dye catch container 154. After completion of the sheath failure test, the sample cement composition 110 may be removed from the test cell 42 and examined to determine the failure path. The time until sheath failure and/or failure rate may be recorded as a function of volume of fluid collected versus time and used to compare the durability of sample cement composition 110 to other sample cement compositions.

In another embodiment, sheath failure may be tested with pressure and temperature variation applied to the sample cement composition 110 by the inner pipe 52. In this embodiment, the variable temperature system 124 of FIG. 4 may be used with a back flow valve (or other suitable circulation and pressure control) coupled to the bottom stem 72b or elsewhere in the fluid return line of the variable temperature system 124. The pump 126 and back flow valve may be used to vary pressure in the inner pipe 52 and thus on the sample cement composition 110.

Figure 6:
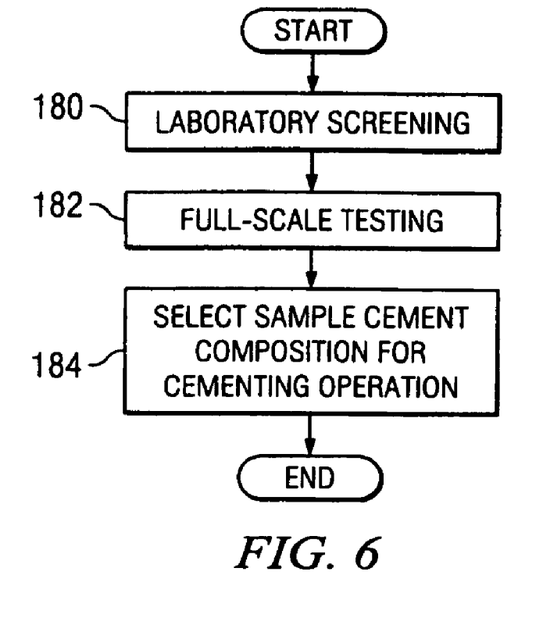
FIG. 6 is a flow diagram illustrating one embodiment of a method for designing a cement composition for a cementing operation in a wellbore.

FIG. 6 illustrates one embodiment of a method for designing a cement composition for a cementing operation in a wellbore. The method begins at step 180 in which laboratory screening of a number of sample cement compositions is performed. In one embodiment, one or more sample cement compositions 110, for example, 10 or 20 or more, may be screened using the laboratory apparatus 10 and test cell 42. The laboratory screening may comprise cement shrinkage, sheath failure or other suitable testing in response to variable and/or cyclic pressure, temperature or other stress conditions. During laboratory screening, new sample cement compositions 110 may be designed based on tested sample cement compositions 110. For example, additives, density and/or strength may be adjusted between sample cement compositions 110.

Based on laboratory screening, a subset of the sample cement compositions may be selected for full-scale testing. In one embodiment, each of the selected sample cement compositions 110 may have performed well under the variable stress conditions expected during curing and operational conditions in the wellbore. For example, the selected sample cement compositions 110 may comprise those with the least cement shrinkage and the greatest durability. In another embodiment, the selected sample cement compositions 110 may comprise the least expensive compositions with suitable performance during testing. The full-scale testing may be performed using a full or other large-scale wellbore model in which cement is pumped between a full-size liner and a pipe, epoxy, sand or other suitable material representing the subterranean formation of the wellbore. The full-scale model may be performance tested by cycling pressure and temperature.

Proceeding to step 182, full-scale testing is performed. Full-scale testing may be performed by cementing a section of a full-size liner in a block representing the rock formation of the wellbore. Full-scale testing may be performed in the field with pressure and temperature changes cycled as described herein to correspond to core and operational conditions.

Step 184 leads to the end of the process by which a large number of sample cement compositions 110 may have been tested under cyclic pressure and temperature conditions to provide an improved one or more cement compositions for full-scale testing or use in the cementing operation in the wellbore. Accordingly, the final slurry design may be enhanced. At step 184, a best performing or other suitable sample cement composition 110 is selected for the cementing operation in the wellbore.

Figure 7:
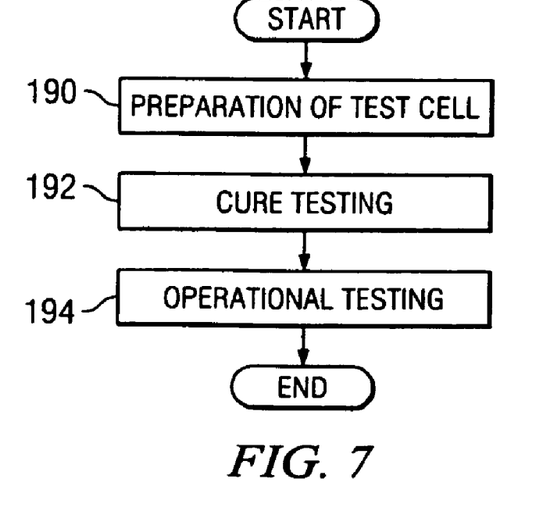
FIG. 7 is a flow diagram illustrating one embodiment of a method for testing a sample cement composition using the test cell of FIG. 2.

FIG. 7 illustrates one embodiment of a method for testing sample cement compositions 110 in test cell 42. The method begins at step 190 in which the test cell 42 is prepared. As previously described, the test cell 42 may be prepared by installing the mesh screen 102 and sand 104, saturating the sand 104 and pouring the sample cement composition 110 into the test chamber 56. Thereafter, the test chamber 56 may be sealed by fastening the top end cap 54a to the outer pipe 50 and connecting the test cell 42 to the variable temperature and/or pressure systems 124 and 160.

Proceeding to step 192, the sample cement composition 110 is tested for cement shrinkage during curing at a curing condition. During curing, the pressure and/or temperature of the outer pipe 50 and/or inner pipe 52 may be controlled to correspond to the curing condition. Cement shrinkage of the sample cement composition 110 may be measured using the pipette 120 and recorded.

At step 194, the sample cement composition 110 is tested for durability at an operational condition. Durability testing may be performed by determining sheath failure or other permeability change of the sample cement composition 110 in response to operational conditions of the wellbore. As described in connection with FIG. 6, the results from shrinkage testing and durability testing may be used to select a cement composition for the cementing operation in the wellbore or used to select a plurality of samples for full-scale or other suitable testing.

A number of embodiments have been described. Nevertheless, it will be understood that various modifications may be made without departing from the spirit and scope of the disclosure. Accordingly, other embodiments are within the scope of the following claims.

What is claimed is:

1. A test cell, comprising:
   a test chamber configured to hold a sample of cement composition for a well bore;
   a variable stress system in communication with the test chamber, the variable stress system configured to apply a cyclical stress to the sample of cement composition;
   wherein the test cell is configured to test a performance of the sample of cement composition for the well bore using the variable stress system; and
   wherein the variable stress system comprises a variable pressure system and a variable temperature system, the variable pressure system and the variable temperature system configured to vary a temperature applied to the sample of cement composition during curing of the sample of cement composition and to vary a pressure and a temperature applied to the sample of cement composition after curing of the sample of cement composition.

2. The test cell of claim 1, wherein, the variable pressure system configured to cycle a pressure applied to the sample of cement composition.

3. The test cell of claim 2, further comprising:
   the variable pressure system configured to vary the pressure applied to the sample of cement composition during curing of the sample of cement composition; and
   wherein the pressure applied to the sample of cement composition during curing of the sample of cement composition represents a curing condition for the well bore.

4. The test cell of claim 2, further comprising:
   the variable pressure device configured to vary the pressure applied to the sample of cement composition after curing of the sample of cement composition; and
   wherein the pressure applied to the sample of cement composition after curing of the sample of cement composition represents an operational condition for the well bore.

5. The test cell of claim 1,
   wherein the temperature applied to the sample of cement composition during curing of the sample of cement composition represents a curing condition for the well bore.

6. The test cell of claim 1,
   wherein the temperature applied to the sample of cement composition after curing of the sample of cement composition represents an operational condition for the well bore.

7. The test cell of claim 1, further comprising:
   an outer pipe forming an outer wall of the test chamber;
   an inner pipe forming an inner wall of the test chamber; and
   wherein the variable stress is applied to the sample of cement composition through the inner pipe.

8. The test cell of claim 7, wherein the outer pipe and the inner pipe are reusable.

9. The test cell of claim 1, wherein the test chamber is less than two feet in length.

10. The test cell assembly of claim 1, wherein performance of the sample of cement composition comprises cement shrinkage and sheath failure of the sample of cement composition.

11. The test cell of claim 1 wherein configured to test a performance for the wellbore comprises configured to test performance under conditions simulating conditions expected in the wellbore.

* * * * *